US005137918A

United States Patent [19]

Weiershausen et al.

[11] Patent Number: 5,137,918
[45] Date of Patent: Aug. 11, 1992

[54] N-(2'-AMINOPHENYL)-BENZAMIDE DERIVATIVES PROCESS FOR THE PREPARATION THEREOF AND PHARMACEUTICAL COMPOSITIONS CONTAINING THEM

[75] Inventors: Ute Weiershausen, Gundelfingen; Gerhard Satzinger, Denzlingen; Karl-Otto Vollmer, Freiburg; Wolfgang Herrmann, Merzhausen, all of Fed. Rep. of Germany

[73] Assignee: Goedecke Aktiengesellschaft, Salzufer, Fed. Rep. of Germany

[21] Appl. No.: 594,592

[22] Filed: Oct. 9, 1990

Related U.S. Application Data

[63] Continuation-in-part of Ser. No. 455,860, Dec. 15, 1989, abandoned, which is a continuation of Ser. No. 39,206, Apr. 16, 1987, abandoned.

[30] Foreign Application Priority Data

Apr. 22, 1986 [DE] Fed. Rep. of Germany ....... 3613571
Jul. 26, 1986 [DE] Fed. Rep. of Germany ....... 3625359

[51] Int. Cl.$^5$ .................... A61K 31/165; C07C 237/42
[52] U.S. Cl. ..................................... 514/616; 514/619; 564/157; 564/168
[58] Field of Search ................. 564/157, 168; 514/616, 514/619

[56] References Cited

U.S. PATENT DOCUMENTS

| 4,004,029 | 1/1977 | Collins et al. | 424/325 |
| 4,642,379 | 2/1987 | Beedle et al. | 564/155 |
| 4,816,485 | 3/1989 | Satzinger et al. | 514/619 |
| 4,857,662 | 8/1989 | Satzinger et al. | 514/619 X |
| 4,933,368 | 6/1990 | Satzinger et al. | 514/619 X |

FOREIGN PATENT DOCUMENTS 3305755 8/1984 Fed. Rep. of Germany ...... 564/168

OTHER PUBLICATIONS

CA 106:19956v, Moser et al., Jan. 1989.
Arsac et al., CA 88:51950j (1977).
Shchel'tsyn et al., Zh Org. Khim 1986, 22(2), 359, 365.

*Primary Examiner*—Carolyn S. Elmore
*Attorney, Agent, or Firm*—Elizabeth M. Anderson

[57] ABSTRACT

The present invention provides substituted N-(2'-aminophenyl)-benzamide derivatives useful for combating neoplastic diseases. The present invention also provides a process for the preparation of these benzamide derivatives, as well as pharmaceutical compositions containing them and methods for using them.

12 Claims, 7 Drawing Sheets

N-(2'-AMINOPHENYL)-BENZAMIDE DERIVATIVES PROCESS FOR THE PREPARATION THEREOF AND PHARMACEUTICAL COMPOSITIONS CONTAINING THEM

CROSS-REFERENCE TO RELATED APPLICATIONS

This is a continuation-in-part of U.S. application, Ser. No. 455,860, filed Dec. 15, 1989 which is a continuation of U.S. application Ser. No. 039206, filed Apr. 16, 1987, now abandoned.

BACKGROUND OF THE INVENTION

The present invention is concerned with new N-(2'-aminophenyl)-benzamide derivatives, a process for the preparation thereof, pharmaceutical compositions containing them, and the use thereof for combatting neoplastic diseases.

German Patent 33 05 755 describes compounds of the general formula I wherein at least one of $R^1$ and $R^3$ is a methyl radical and the other symbols $R^1$, $R^2$, and $R^3$, which can be the same or different, represent hydrogen atoms or methyl radicals, as being effective for combatting malignant, proliferative, and autoimmune diseases, 4-amino-N-(2'-aminophenyl)-benzamide and its N-monomethyl derivative being said to be especially effective.

Surprisingly, we have now found that the basic p-amino function, which was initially thought to be pharmacologically essential, is not responsible for the therapeutic effectiveness of these compounds but rather that the absence thereof or a chemical change or thereof into neutral-reacting groups by substitution or replacement thereof by nonbasic radicals gives rise to effective compounds with a superior compatibility.

SUMMARY AND DETAILED DESCRIPTION

The present invention concerns new N-(2-aminophenyl)benzamide derivatives for the therapy of malignant, proliferative, and autoimmune diseases which have the general formula II wherein R is a lower acylamino radical, including those with up to four carbon atoms which are optionally substituted with hydroxyl groups.

The term lower acylamino is wherein X is hydrogen or a group of from one to three carbon atoms which may be unsubstituted or substituted by one or more hydroxyl groups.

Preferred compounds of general formula (II) which contain a lower acylamino radical R include the
1) 4-acetamino-N-(2'-aminophenyl)-benzamide,
2) 4-isobutyrylamino-N-(2'-aminophenyl)-benzamide,
3) 4-formylamino-N-(2'-aminophenyl)-benzamide,
4) 4-(β-hydroxypropionylamino)-N-(2'-aminophenyl)-benzamide, and
5) 4-glycolamino-N-(2'-aminophenyl)-benzamide.

The 4-acylamino compounds 1) to 5) are new. The compound in which R is a hydrogen atom has been described (Beilstein, 13, Main Work, p. 20) without mention of its pharmacological action.

The present invention is also concerned with the use of compounds of general formula (II), wherein R can also be a hydrogen atom, for combatting neoplastic diseases.

The compounds of general formula (II) can be prepared by reacting a compound of the general formula IIIa wherein R has the same meaning as above and A is a reactive acid group, with a compound of the general formula IIIb wherein X is an amino group provided with a protective group or is a nitro group, to give a compound of the general formula IV wherein X and R have the above-given meanings, which is converted into a compound of general formula (II) either by reduction or by splitting off the protective group.

The reaction of compounds of general formula (IIIa) with compounds of general formula (IIIb) takes place in known manner. The reactive acid group A can, in particular, be an acid halide, acid anhydride, imidazolide, or ester group which permits a reaction with the amino group. Thus, A is preferably a halogen atom or an imidazolyl, acyl or lower alkoxy radical.

The protective group for X is one of those conventional in peptide chemistry, for example, a benzyl or carbobenzoxy radical. The reduction can be carried out with hydrogen for the use of an appropriate catalyst, for example, platinum or palladium, in such a manner that, on the one hand, the free nitro group is reduced to give a primary amino group and, on the other hand, the protective group on the amino group is split off hydrogenolytically.

The active materials according to the present invention are advantageously administered in the form of a pharmaceutical composition which contains the active material in free form or in the form of a mixture with an appropriate pharmaceutical organic or inorganic solid or liquid carrier material, which can be administered topically, enterally, for example, orally or rectally, parenterally, for example, intramuscularly or intravenously. For the preparation of such compositions, there can be used those materials which do not react with the new compounds according to the present invention, for example, gelatine, lactose, starch, stearyl alcohol, magnesium stearate, talc, vegetable oils, benzyl alcohol, propylene glycols, petroleum jelly or other pharmaceutical carriers.

The pharmaceutical compositions can be in the form of, for example, tablets, dragees, capsules, suppositories, salves or creams or in liquid form as suspensions or emulsions. If necessary, they are sterilized and/or contain adjuvants, such as preserving agents, stabilizing agents, wetting agents or emulsifiers, solubilizing agents or salts for changing the osmotic pressure or buffers. They can also contain further active materials.

The dosage employed depends upon the nature of the disease to be treated therapeutically and upon individual factors. In general, dosages of from 10 to 300 mg and especially of from 20 to 50 mg are administered. In special cases, the individual dosage can also be higher.

DRAWINGS

FIG. 1 is the AUC, rat, after administration of 4-acetamino-N-(2'-aminophenyl)benzamide. The * is intragastral administration (2 mg/kg; 10 mg/kg; 50 mg/kg). The * is intravenous administration (10 mg/kg).

FIGS. 2 and 3 show graphically that the active material of the present invention is characterized, in comparison with the standard, by a longer half-life time so that it is possible to maintain a cytostatic activity level over a comparatively long period of time. In FIG. 2 the average plasma level of 4-amino-N-(2'-aminophenyl)-benzamide in rats after single administration of 10 mg/kg intragastrally (n=4). The half-life (t½) is about 15 minutes.

From FIG. 4 it is evident that 5-acetamino-N-(2'-aminophenyl)-benzamide affects tumor growth in a dose-dependent manner with almost complete tumor growth inhibition in the highest dose group.

BIOLOGICAL DATA

4-Acetamino-N-(2'-aminophenyl) benzamide was used as an example of a compound according to the present invention and compared with 4-N-(2'-aminophenyl)-benzamide as standard, the outstanding inhibition action of which against various experimental tumors in vitro and in vivo is known. The testing was carried out in vivo with SD-rats against MNU-induced mammary adenocarcinoma and acetoxymethylmethylnitrosamine-induced (AMMN-induced) colon adenocarcinoma. The testing was carried out in vitro in the "colorimetric-cytotoxicity assay" using L1210 and mammary adenocarcinoma 16C tumor cells. In this test system, substances with $ID_{50}$ values of $\leq 250$ μg/mL are assessed as being cytostatically active.

It could be shown (see the following Table 1) that the active material 4-acetamino-N-(2'-aminophenyl)-benzamide according to the present invention:
1) acts outstandingly cytostatically; and
2) has a cytostatic activity which is about the same or better as that of the comparison standard.

TABLE 1

| Test Substance | $ID_{50}$ μg/mL |
|---|---|
| L1210 Colorimetric Cytotoxicity Assay | |
| (A) 4-Acetamino-N-(2'-aminophenyl)-benzamide) | 3.75 |
| (B) 4-Amino-N-(2'-aminophenyl)-benzamide | 2.78 |
| (C) 4-Methylamino-N-(2'-aminophenyl)-benzamide | 4.04 |
| Mamma Adenocarcinoma 16C Cytotoxicity Assay | |
| (A) 4-Acetamino-N-(2'-aminophenyl)-benzamide | 0.73 |
| (B) 4-Amino-N-(2'-aminophenyl)-benzamide | 0.69 |
| 4-Isobutyrylamino-N-(2'-aminophenyl)-benzamide | 0.32 |
| 4-Formylamino-N-(2'-aminophenyl)-benzamide | 0.40 |
| 4-(β-Hydroxypropionyl)amino-N-(2'-aminophenyl)-benzamide | 0.77 |
| 4-Glycoloylamino-N-(2'-aminophenyl)-benzamide | 0.62 |

Surprisingly, we have found that the active material according to the present invention, 4-acetamino-N-(2'-aminophenyl)-benzamide, is considerably less toxic in the case of acute intragastral administration than the comparison standard. This was demonstrated in an orientating experiment (n=4) on male mice for the determination of the $LD_{50}$ with a 7-day period of observation. The results are shown in the following Table 2:

TABLE 2

| Test Substance | $LD_{50}$ mg/kg |
|---|---|
| (A) 4-Acetamino-N-(2'-aminophenyl)-benzamide | 1600 |
| (B) 4-Amino-N-(2'-aminophenyl)-benzamide | 625 |

In pharmacokinetic experiments on rats, a reduced resorption as a possible cause for the substantially improved acute compatibility of the active material according to the present invention in comparison with the standard could be excluded: the intestinal resorption of the substance took place quickly, completely, and dosage-linearly.

Figure 1:
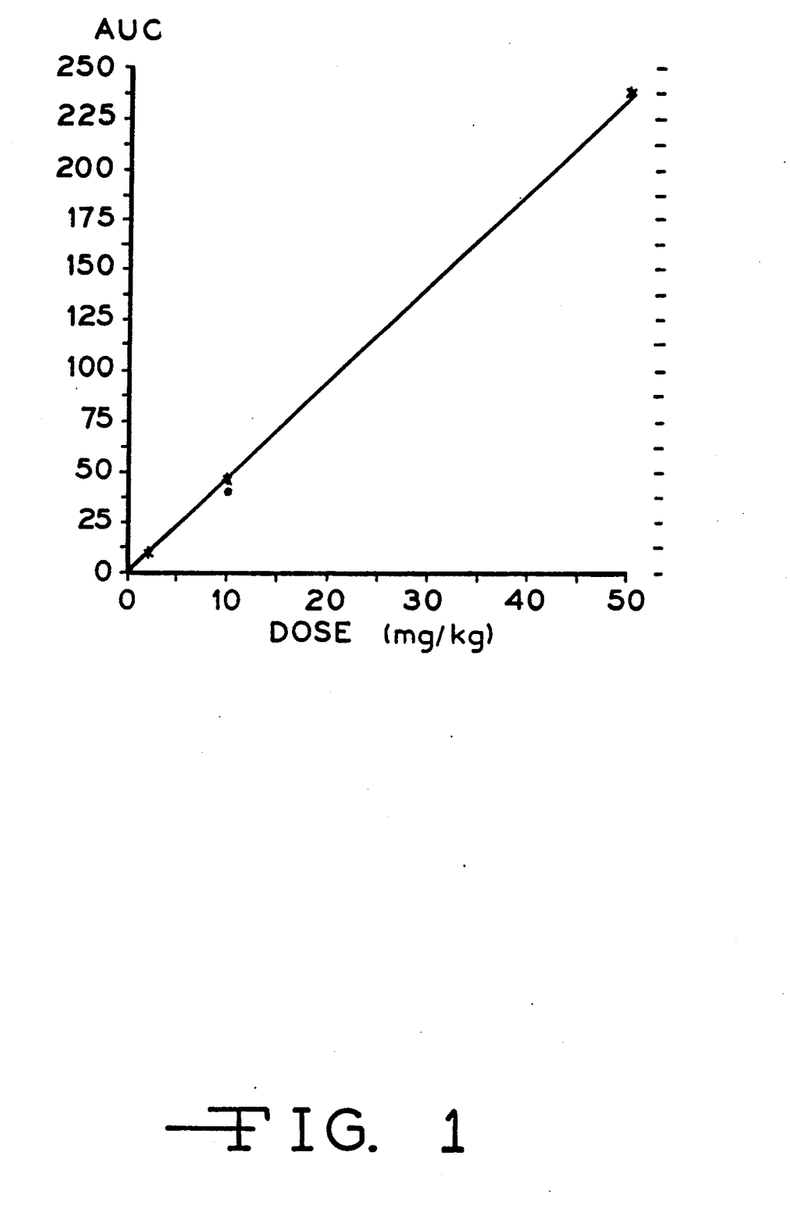
FIG. 1 shows graphically that there is not statistically significant difference of the AUCs (area under the plasma concentration-time curve) found after intravenous and intragastral administration to rats at 10 mg/kg.

The bioavailability of the active material according to the present invention is 100%. No statistically significant difference of the AUC's was found after intravenous and intragastral administration to rats of 10 mg/kg. This is shown graphically in FIG. 1 of the accompanying drawings.

Figure 2:
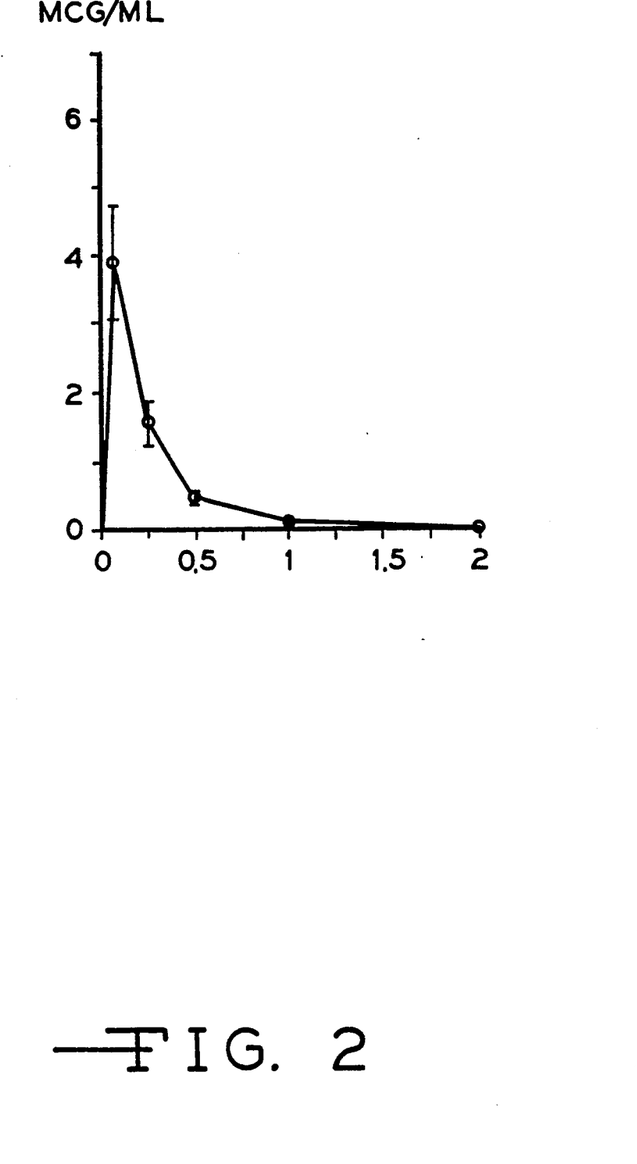
Figure 3:
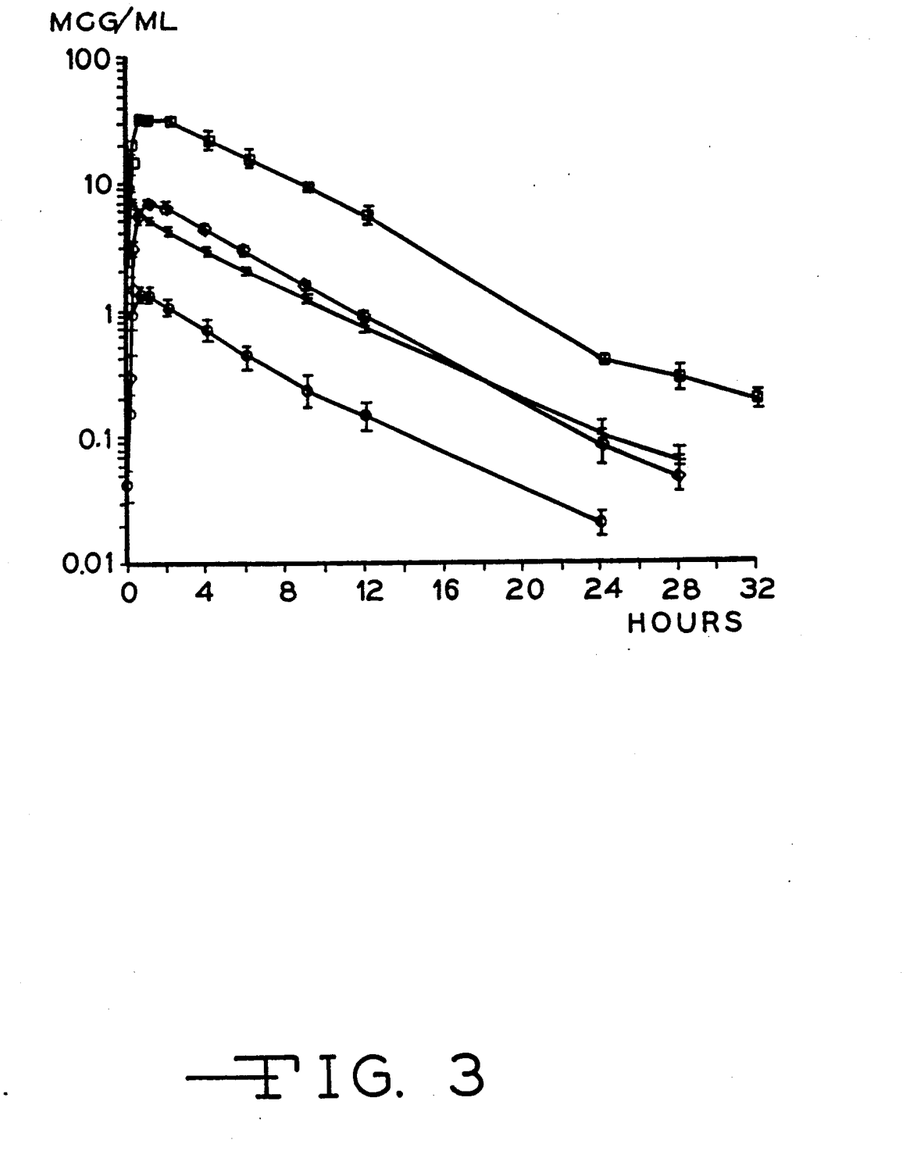
FIG. 3 shows the average plasma level of 4-acetamino-N-(2'-aminophenyl)-benzamide in rats after single administration. + stands for 10 mg/kg intravenously (n=5), ○ stands for 2 mg/kg intragastrally (n=5), ● for 10 mg/kg intragastrally (n=6), □ stands for 50 mg/kg intragastrally (n=5). Half-life (t½) is about 4.2–4.5 hours.

Besides its better compatibility, the active material according to the present invention is also characterized, in comparison with the standard, by the longer half-life time (see FIGS. 2 and 3 of the accompanying drawings) so that it is possible to maintain a cytostatic activity level over a comparatively long period of time.

Figure 4:
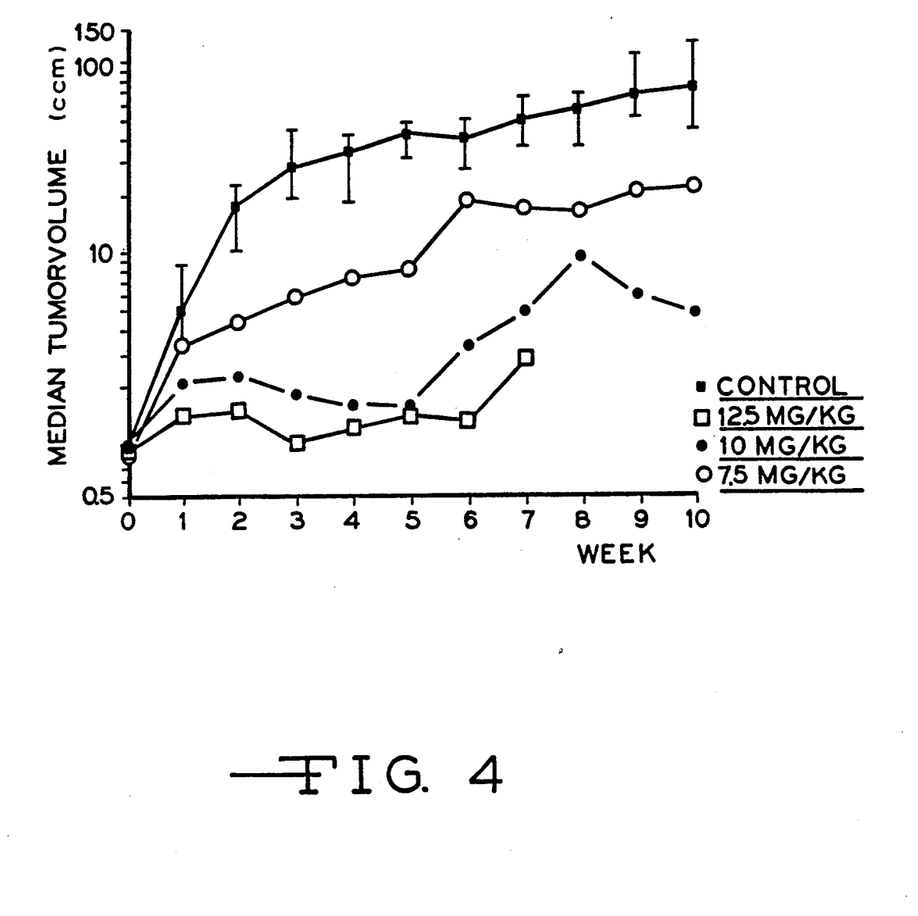
FIG. 4 shows the activity of 4-acetamino-N-(2'-aminophenyl)-benzamide against methylnitrosurea-induced (MNU-induced) mammary adenocarcinoma in SD rats. is control; □ is 12.5 mg/kg; ● is 10 mg/kg; and ○ is 7.5 mg/kg.
Figure 5:
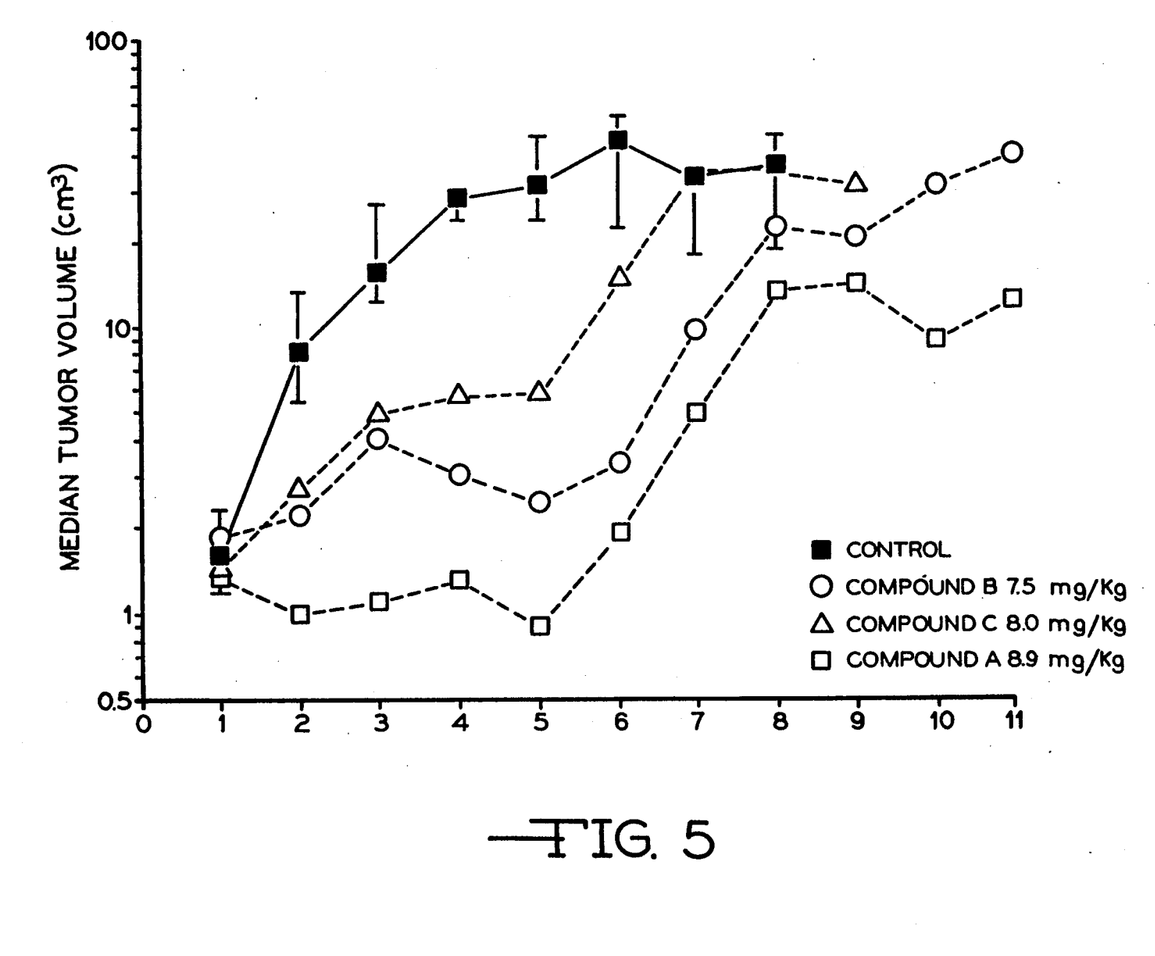
FIGS. 5 and 6 show the antineoplastic effect of compounds A, B, C at equimolar doses (33 μmol/kg/day); is control; Δ is compound C (8.0 mg/kg), ○ is compound B (7.5 mg/kg), and □ is compound A (8.9 mg/kg).
Figure 6:
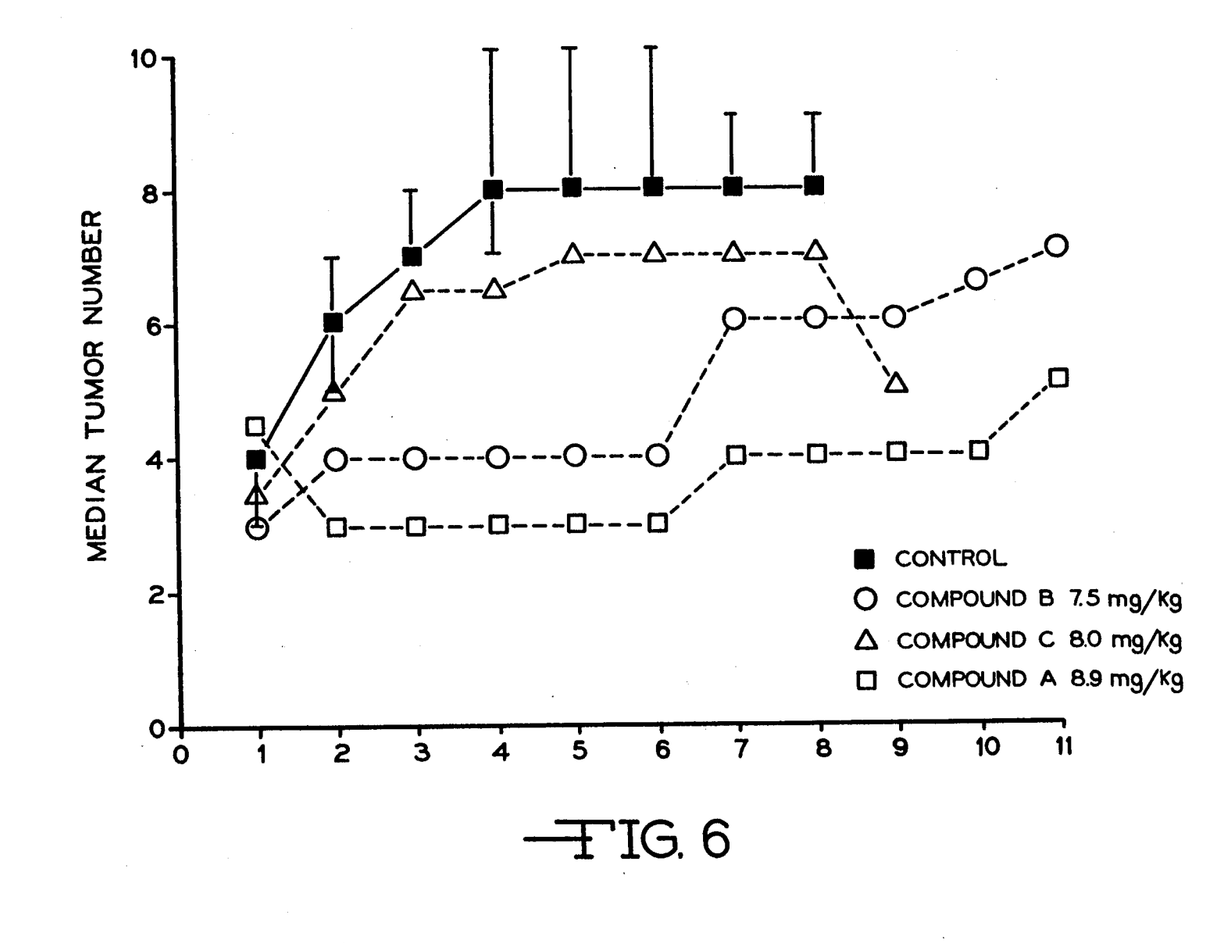

The in vivo activity of 4-acetamino-N-(2'-aminophenyl)-benzamide was tested against primary mammary adenocarcinoma induced by 3 single IV administrations of methylnitrosurea on Days 50, 71, and 92 following birth in female SD rats. As soon as tumor volumes $\geq 0.8$ cm$^3$ were reached, test animals were randomized and therapy was started. The compounds A, B, and C were administered intragastrally, 5 times/week for 5 weeks. The doses of compounds A, B, and C were respectively: A: 7.5, 8.9, 10.0 and 12.5 mg/kg/day; B: 7.5 mg/kg/day; C: 8.0 mg/kg/day. Median tumor volumes and numbers were determined weekly and compared with untreated controls. At equimolar doses (33 $\mu$mol/kg/day) the acetyldinaline (compound A) shows the highest antineoplastic effect, as can be seen from FIGS. 5 and 6. From FIG. 4 it is evident that 4-acetamino-N-(2'-aminophenyl)benzamide affects tumor growth in a dose-dependent manner with almost complete tumor growth inhibition in the highest dose group.

The activity of the compounds A, B, and C was tested in vivo against AMMN-induced colon adenocarcinoma. Male SD-rats were given 2 mg/kg/week acetoxymethylmethylnitrosamine (AMMN) intrarectally for a period of 10 weeks for tumor induction. Animals with manifest tumors were assigned randomly to the test groups. The therapy scheme is given in Table 3.

TABLE 3

| Group | Number of Animals | Test Substance | Dose$^a$ (mg/kg/day) | Duration of Therapy (Weeks) | Total Dose (mg/kg) |
|---|---|---|---|---|---|
| K1 | 15 | — | — | — | — |
| K2 | 20 | — | — | 10 | 0 |
| 3 | 15 | (B) | 10 | 10 | 500 |
| 4 | 15 | (B) | 7.7 | 10 | 385 |
| 5 | 15 | (B) | 5.9 | 10 | 295 |
| 6 | 5 | (A) | 11.9 | 10 | 595 |
| 7 | 15 | (A) | 9.1 | 10 | 455 |
| 8 | 15 | (A) | 7.0 | 10 | 350 |
| 9 | 15 | (A) | 5.3 | 10 | 265 |
| 10 | 15 | (C) | 13.8 | 10 | 690 |
| 11 | 15 | (C) | 10.6 | 10 | 530 |
| 12 | 15 | (C) | 8.2 | 10 | 410 |
| 13 | 10 | (C) | 6.2 | 10 | 310 |

Figure 7:
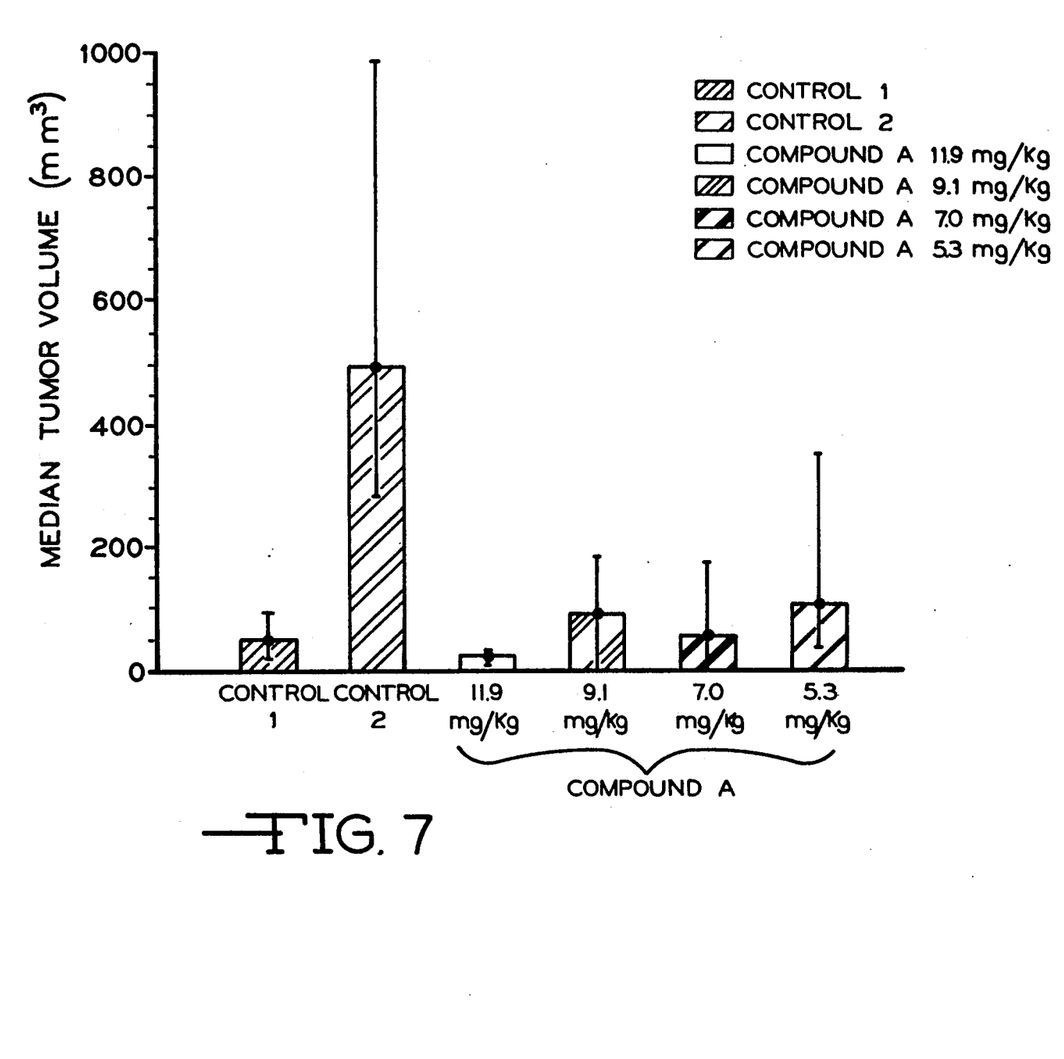
FIG. 7 shows the growth inhibition of AMMN-induced colon adenocarcinoma with compound A at different doses (5.3, 7.0, 9.1, and 11.9 mg/kg).

$^a$Application via gastric tube, 5 days per week
(A) = Compound A, (B) = Compound B, (C) = Compound C The animals were examined twice daily. After the 10-week treatment period, the animals were sacrificed and a total necropsy performed. All tumors were individually measured and their volumes added to a total tumor volume. All three compounds show an antineoplastic effect, compounds B and A being very efficient. The optimum dose of compound B (5.9 mg/kg/day=26 $\mu$mol/kg/day) resulted in arrest of tumor growth (relative median tumor volume T/C: 10.6%). The equimolar dose of compound A (7.0 mg/kg/day) also completely inhibited further growth of colon carcinoma in the medium (T/C 11.1%). Furthermore, with a dose of compound A being 11.9 mg/kg, the growth inhibition is much less (T/C about 5%), as can be seen from FIG. 7.

Thus, the compounds according to the present invention are, in comparison with the comparison standard, 4-N-(2'-aminophenyl)-benzamide, cytostatics which are clearly improved in important biological parameters and, at the same time, are equally effective cytostatics against L1210 leukemia cells and AMMN-induced colon carcinoma and have better activity against mammary adenocarcinoma 16C.

Therefore, the new compounds according to the present invention are of therapeutic importance and are agents for the systemic and/or topical treatment of malignant neoplasias, for the treatment of benign proliferative diseases, and for the treatment of disturbances of the cellular and humoral immune system.

There is also included the possibility of a combination with therapeutics from which it is to be expected that they strengthen and favorably influence the desired effects.

The following examples are given for the purpose of illustrating the present invention:

EXAMPLE 1

4-Acetamino-N-(2'-aminophenyl)-benzamide 30 g (0.1 mole) N-(2'-aminophenyl)-4-acetylaminobenzamide are hydrogenated under standard conditions in tetrahydrofuran in the presence of 10% palladium charcoal. After removal of the catalyst, the filtrate is concentrated to about one-quarter of its volume and the precipitate obtained is filtered off with suction. If desired, the product can be recrystallized from methanol/tetrahydrofuran (1:1 v/v). Yield 18.6 g (69% of theory); m.p. 243.7° C.

The N-(2'-nitrophenyl)-4-acetylaminobenzamide used as starting material is prepared as follows: 41.3 g (0.33 mole) oxalyl chloride are added dropwise at 0°–5° C., with the exclusion of moisture, to a solution of 60.3 g (0.83 mole) dimethylformamide in 1.5 L dry ethyl acetate. After stirring for 30 minutes at this temperature, 44.8 g (0.25 mole) 4-acetamidobenzoic acid, together with 27.7 g (0.35 mole) pyridine, are added thereto and the ice bath is removed. After stirring for 3 hours at ambient temperature, the reaction mixture is mixed with a solution of 38 g (0.28 mole) o-nitroaniline and 27.7 g (0.35 mole) pyridine in 30 mL dry ethyl acetate. After stirring for 15 hours at ambient temperature, the reaction mixture is mixed with 500 mL 1N aqueous sodium hydroxide solution, the phases are separated and the aqueous phase is shaken out three times with 150 mL amounts of ethyl acetate. The combined organic phases are washed neutral with water, dried over anhydrous sodium sulfate, and concentrated to about one-third. The precipitate obtained is filtered off with suction and purified either by recrystallization or by column chromatography. Yield 15 g (20% of theory); m.p. 205.8° C.

EXAMPLE 2

4-($\beta$-Hydroxypropanoyl)-amino-N-(2'-aminophenyl)-benzamide 2 g (4.76 mMole) N-(2, nitrophenyl) 4-(3-benzyloxypropanoylamino)-benzamide are dissolved in 300 mL ethanol and hydrogenated in the presence of 1 g 5% palladium charcoal at 80° C. for 6 hours in an autoclave. After filtration, the solvent is removed and the residue is purified by column chromatography (silica gel; methylene chloride/methanol 9:1 v/v). Yield 0.8 g (56% of theory); m.p. 197.7° C.

The compounds used as starting materials are prepared as follows:

4-(3-Benzyloxypropanoylamino)-benzoic acid 8.09 g (59 mMole) p-aminobenzoic acid, together with 4.98 g (63 mMole) pyridine, are dissolved in 100 mL dioxan and mixed at 15° C. with 11.7 g (59 mMole) 3-benzyloxypropionic acid chloride (J.C.S., Perkin I, 1976, 2229) in 2 mL dioxan. After stirring for 3 hours at ambient temperature, the reaction mixture is mixed with 300 mL water. The precipitate obtained is filtered off with suction, washed with water, and dried. Without further purification, the product is used in the next step. Yield 15.7 g (89% of theory); m.p. 162°-164° C. sinters; >200° C. decomposition.

N-(2'-Nitrophenyl)-4-(3-benzyloxypropanoylamino)-benzamide is prepared analogously to Example 1 using 12 g (40.1 mMole) 4-(3 benzyloxypropanoylamino)-benzoic acid, 6.6 g (0.13 mMole) oxalyl chloride, 9.7 g (0.13 mole) dimethylformamide, 2×4.5 g pyridine, 6.1 g (44.1 mMole) o-nitroaniline, and 280 mL dry ethyl acetate. The crude product is purified by column chromatography (silica gel; ethyl acetate/n hexane 1:5-1:1 v/v). Yield 3.5 g (21% of theory); m.p. 140° C.

EXAMPLE 3

4-Isobutyrylamino N-(2'-aminophenyl) benzamide 13.1 g (40 mMole) N-(2'-nitrophenyl)-4-isobutyrylaminobenzamide are hydrogenated under standard conditions in 400 mL tetrahydrofuran in the presence of 10% palladium charcoal. After concentrating the solvent to 120 mL, the precipitated crystals are filtered off with suction. Yield 10.2 g (86% of theory); m.p. 247.6° C.

The compounds used as starting materials are prepared as follows:

4-Isobutyrylaminobenzoic acid 50 g (0.36 mole) p-aminobenzoic acid and 30 g (0.38 mole) pyridine are dissolved in 600 mL dioxan and mixed dropwise at 15° C., with the exclusion of moisture, with 40.5 g (0.38 mole) isobutyric acid chloride. After stirring for 2 hours at ambient temperature, 500 mL water are added thereto, with vigorous stirring. The precipitate obtained is filtered off with suction, washed with water, dried, and recrystallized from diisopropyl ether/ethyl acetate (3:4 v/v). Yield 22 g (30% of theory); m.p. 241° C.

N-(2'-Nitrophenyl)-4-isobutyrylaminobenzamide is prepared under the reaction conditions given in Example 5: after the addition of pyridine/o-nitroaniline, the reaction solution is stirred for 15 hours at ambient temperature and for 5 hours at boiling temperature, the following components being used: 54.6 g (74.68 mMole) dimethylformamide, 1.5 L dry ethyl acetate, 37.3 g (29.42 mMole) oxalyl chloride, 47 g (22.63 mMole) 4-isobutyrylaminobenzoic acid, 34.4 g (24.89 mMole) o-nitroaniline, and 25.6 g (32.36 mMole) pyridine. The product is recrystallized from ethyl acetate. Yield 13.3 g (18% of theory); m.p. 237.6° C.

EXAMPLE 4

4-Glycoloylamino-N-(2'-aminophenyl)-benzamide 6.08 g (15 mMole) N-(2'-nitrophenyl)-4-benzyloxyacetaminobenzamide are dissolved in 400 mL ethanol and 200 mL tetrahydrofuran and hydrogenated in an autoclave for 19 hours at 80° C. and 50 bar hydrogen pressure in the presence of 3 g 15% palladium charcoal. The contents of the autoclave are filtered while still hot and the colorless filtrate is evaporated to dryness. The crystalline residue is recrystallized from 800 mL methanol. Yield 2.6 g (63.2% of theory); m.p. 221°-223° C.

The starting materials used are prepared as follows:

4-Benzyloxyacetaminobenzoic acid 35.7 g (0.26 mole) p-aminobenzoic acid, together with 23.7 g (0.30 mole) pyridine, are dissolved in 420 mL dioxan and mixed dropwise at 15° C. with 51.7 g (0.28 mole) benzyloxyacetic acid chloride (Heterocyclic Chem., 15, 601, 1978). After stirring for 2 hours at ambient temperature, the reaction mixture is mixed with 300 mL water. The precipitate obtained is filtered off with suction, washed with water, and dried. The product is used for the next step without further purification. Yield 63 g (98.3% of theory); m.p. 178°-179° C.

N-(2'-Nitrophenyl)-4-benzyloxyacetaminobenzamide 28.5 g (0.39 mole) dry dimethylformamide in 910 mL dry ethyl acetate are mixed dropwise at 2° C., under an atmosphere of nitrogen, with 21.5 g (0.17 mole) oxalyl chloride. After stirring for 30 minutes at 2°-5° C., a suspension of 37.2 g (0.13 mole) 4-benzyloxyacetaminobenzoic acid and 14.4 g (0.18 mole) pyridine in 65 mL ethyl acetate are added thereto and the ice bath is removed. After stirring for 2.5 hours at ambient temperature, the reaction mixture is mixed with a solution of 19.8 g (0.14 mole) o-nitroaniline and 14.4 g (0.18 mole) pyridine in 65 mL ethyl acetate. After stirring for 1 hour at ambient temperature, the reaction mixture is heated to the boil for 3 hours. After cooling, it is mixed with 500 mL 1N aqueous sodium hydroxide solution and the phases are separated. The aqueous phase is shaken out twice with ethyl acetate. The combined organic phases are washed neutral with water and dried over anhydrous sodium sulfate. The solvent is evaporated to 150 mL and the precipitated crystals are filtered off with suction and recrystallized from 700 mL ethanol. Yield 13 g (24.7% of theory); m.p 128°-130° C.

EXAMPLE 5

N-(2'Aminophenyl)-4-formylamino-benzamide 1.92 g (67.3 mMole) N-(2'-nitrophenyl) 4-formylamidobenzamide are hydrogenated under standard conditions in 500 mL tetrahydrofuran in the presence of 10% palladium charcoal. After removal of the catalyst, the solvent is removed in a vacuum and the crystalline residue is recrystallized from tetrahydrofuran/diisopropyl ether (1:1 v/v). Yield 1.5 g (88.5% of theory); m.p. 197.7° C. (decomp.).

The starting material is prepared in the following manner:

N-(2'-Nitrophenyl)-4-formylamidobenzamide 7.9 g (0.11 mole) dimethylforamimide and 80 mL dry ethyl acetate are mixed dropwise at 0°-5° C., under an atmosphere of nitrogen, with 5.9 g (46.8 mMole) oxalyl chloride. After stirring for 30 minutes at this temperature, the reaction mixture is mixed with 5.95 g (36 mMole) formyl-4-amidobenzoic acid (Chem. Ber., 23, 3625, 1890; Beilsteins Handbuch der Organidschen Chemie, pub. Springer Verlag, 1931, Vol. 14, p. 432) and 4.3 g (54 mMole) pyridine and the ice bath is removed.

After stirring for 3 hours at ambient temperature, the solution is mixed with 5.47 g (39.6 mMole) o-nitroaniline in 15 mL dry ethyl acetate and stirred for 15 hours at ambient temperature. The solution is subsequently rendered alkaline with ammonia, washed with water, and dried over anhydrous sodium sulfate. After removal of the solvent, a crystalline residue remains behind which is recrystallized from ethyl acetate. Yield 1.5 g (14.6% of theory); m.p. 237.6° C.

We claim:

1. A compound of the formula wherein R is a lower acylamino group wherein X is hydrogen or a group of one to three carbon atoms unsubstituted or substituted by one or more hydroxyl groups.

2. A compound according to claim 1 and being 4-acetamino-N-(2'-aminophenyl)-benzamide.

3. A compound according to claim 1 and being 4-isobutyrylamino-N-(2'-aminophenyl)-benzamide.

4. A compound according to claim 1 and being 4-formylamino-N-(2'-aminophenyl)-benzamide.

5. A compound according to claim 1 and being 4-($\beta$-hydroxypropionylamino)-N-(2'-aminophenyl)-benzamide.

6. A compound according to claim 1 and being glycoloylamino-N-(2'-aminophenyl)-benzamide.

7. A pharmaceutical composition effective for treating mammary adenocarcinoma 16C comprising a therapeutically effective amount of a compound according to claim 1 in combination with a pharmaceutically acceptable carrier.

8. A pharmaceutical composition effective for treating L1210 leukemia comprising a therapeutically effective amount of a compound according to claim 1 in combination with a pharmaceutically acceptable carrier.

9. A pharmaceutical composition effective for treating colon adenocarcinoma comprising a therapeutically effective amount of a compound according to claim 1 in combination with a pharmaceutically acceptable carrier.

10. A method for treating mammary adenocarcinoma 16C in mammals which comprises administering to a mammal in need thereof a pharmaceutical composition according to claim 7 in unit dosage form.

11. A method for treating L1210 leukemia in mammals which comprises administering to a mammal in need thereof a pharmaceutical composition according to claim 8 in unit dosage form.

12. A method for treating colon adenocarcinoma in mammals which comprises administering to a mammal in need thereof a pharmaceutical composition according to claim 9 in unit dosage form.

* * * * *